United States Patent [19]

Knifton

[11] 3,932,484

[45] Jan. 13, 1976

[54] PREPARATION OF MONOCARBOXYLATED CYCLODODECA DERIVATIVES

[75] Inventor: John F. Knifton, Poughquag, N.Y.

[73] Assignee: Texaco Inc., New York, N.Y.

[22] Filed: Apr. 22, 1974

[21] Appl. No.: 462,832

[52] U.S. Cl............................ 260/468 R; 260/468 N
[51] Int. Cl.$^2$.......................................... C07C 67/38
[58] Field of Search.................... 260/468 R, 468 N

[56] References Cited
UNITED STATES PATENTS

| | | | |
|---|---|---|---|
| 2,675,390 | 4/1954 | Rosenblatt...................... | 260/514 R |
| 3,437,676 | 4/1968 | von Kutepow et al......... | 260/468 M |
| 3,700,706 | 10/1972 | Butter............................ | 260/468 M |

FOREIGN PATENTS OR APPLICATIONS

| | | | |
|---|---|---|---|
| 1,028,707 | 4/1966 | United Kingdom............ | 260/468 M |
| 2,114,544 | 10/1971 | Germany........................ | 260/468 M |

OTHER PUBLICATIONS

Itatani et al., I. & E. C. Prod. Res. Develop., Vol. II, No. 2, pp. 146–155, (1972).
J. A. C. S., Vol. 85, pp. 1691–1692, (1963).
Chemical Abstracts, Vol. 67, 53652d, (1967), (Abstract of Fr. Pat., No. 1,459,643).

*Primary Examiner*—Robert Gerstl
*Attorney, Agent, or Firm*—T. H. Whaley; C. G. Ries; Bernard Marlow

[57] ABSTRACT

This invention concerns an improved process for preparing monocarboxylated derivatives of cyclododecatriene by the catalytic addition of carbon monoxide using certain homogeneous, experimentally selected, three component, ligand-stabilized, platinum(II) or palladium(II)-Group IVB metal halide catalyst compositions.

Optionally, in the case of certain ligand-stabilized, platinum(II) halide-Group IVB metal halide catalyst complexes, the above carboxylated reaction mixture containing alkyl cyclododecadiene carboxylate can be purged of carbon monoxide, hydrogen can be passed into the reaction mixture, the reaction mixture pressurized in a hydrogen atmosphere and the carbon-to-carbon double bonds in said alkyl cyclododecadiene carboxylate intermediate reduced.

4 Claims, No Drawings

PREPARATION OF MONOCARBOXYLATED CYCLODODECA DERIVATIVES

This invention most broadly concerns a simplified catalytic process for preparing monocarboxylated cyclododecatriene derivatives using selected homogeneous, three-component ligand-stabilized, palladium(II) or platinum(II) dihalide-Group IVB halide catalyst complexes under relatively mild reaction conditions of temperature and pressure.

derivative by the addition of carbon monoxide and a lower alkanol (See Step 1), and then by replacing the CO atmosphere by hydrogen, and optionally using the same homogeneous catalyst, to reduce said monoalkyl unsaturated 4,8-cyclododecadiene-1-carboxylate ester to the monoalkyl ester of cyclododecanecarboxylate (See Step 2). After separating the catalyst, the cyclododecanecarboxylate ester is converted to lauryl lactam by treatment with nitrosylsulphuric acid (Step 3). Polymerization of lauryl lactam yields the polyamide known as Nylon-12 (Step 4).

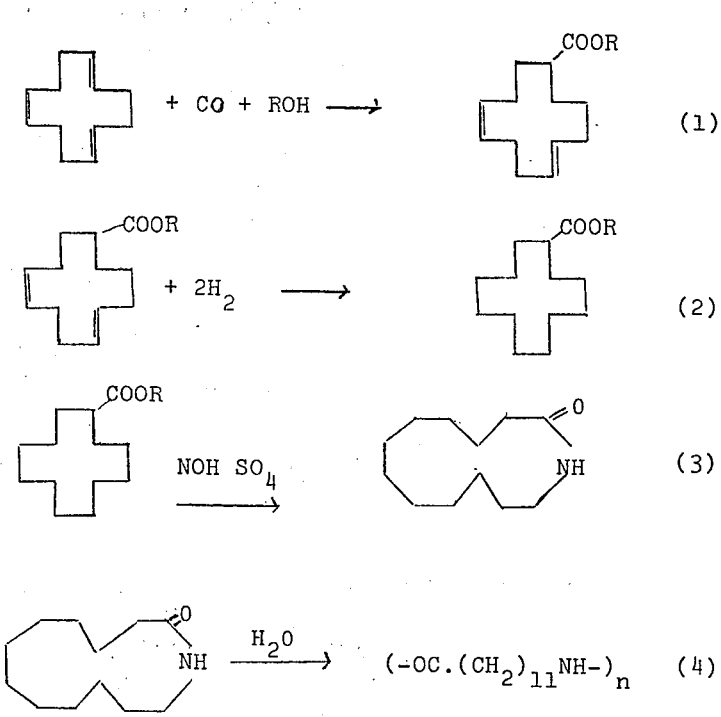

SCHEME I

More particularly, this invention relates to the preparation of the monoalkyl esters of cyclododecadiene carboxylate in good yield from the higly selective catalytic addition of carbon monoxide to 1,5,9-cyclododecatriene in the presence of alkanols and of certain catalyst complexes, followed by hydrogenation of said monoalkyl esters of cyclododecadiene carboxylate.

BACKGROUND OF THE INVENTION

The monoalkyl cyclododecadienecarboxylates are useful generally as organic intermediates, and particularly after reduction of both double bonds, as intermediates in the preparation of lauryl lactam, a useful precursor to Nylon-12. Nylon-12 is a polyamide having excellent mechanical properties such as hardness, tensile strength, resistance to abrasion combined with low sensitivity toward water and low density. Present applications include coatings for cables and textiles and mouldings for automobiles. One contemplated route to Nylon-12,* starting from 1,5,9-cyclododecatriene, is to first carboxylate said triene in the presence of a suitable homogeneous, ligand-stabilized, platinum(II) or palladium(II)-Group IVB metal halide catalyst to form the monoalkyl 4,8-cyclododecadiene-1-carboxylate ester

*See K. Bittler et al., Angew.Chem.internat.Ed., 7,329(1968)

DEFINITIONS

Carboxylation as used herein refers to the process of preparing fatty acid ester derivatives of 1,5,9-cyclododecatriene by the catalytic addition of carbon monoxide plus an alkanol to the 1,5,9-cyclododecatriene.

Conversion as defined throughout this disclosure represents the extent of transformation of the 1,5,9-cyclododecatriene to other products. Conversion is expressed in mole percent and is calculated by dividing the amount of said "triene" consumed during carboxylation by the amount of "triene" charged and multiplying the quotient by 100.

Yield as defined herein, represents the efficiency of the empirically selected three component palladium (II) or platinum(II) catalyst complexes in carboxylating 1,5,9-cyclododecatriene to the desired monoalkyl cyclododecadienecarboxylate esters relative to other undesired by-products. Yield is also expressed as mole percent, and is calculated by determining the amount of cyclododecadienecarboxylate ester formed, divided by the amount of said ester which theoretically can be formed and multiplying the quotient obtained by 100.

Analytical procedures used to determine conversions to desired or undesired products include standard analytical techniques such as gas chromatography (g.c.), infrared (i.r.), elemental analysis, nuclear magnetic resonance (n.m.r.) among others. Unless otherwise stated, all percentages are mole percent, rather than percentages by weight or volume, and all temperatures are in centigrade rather than fahrenheit.

Selectivity as used in this specification refers to efficiency in producing monoalkyl cyclododecadienecarboxylate esters compared to other undesired di- or tricarboxylates. Selectivity is calculated by determining the mole percent of monoalkyl cyclododecadienecarboxylate formed divided by the mole percent of all carboxylates formed multiplied by 100.

CATALYSTS, REACTANTS AND REACTION PARAMETERS

The three component, ligand stabilized, homogeneous platinum(II) or palladium(II)-Group IVB catalyst complexes are known in the literature, albeit not for this purpose, and methods for their preparation have been described.* One convenient mode or preparation in situ is to mix a ligand stabilized platinum(II) or palladium(II) halide, such as $PtCl_2[As(C_6H_5)_3]_2$ with a large molar excess of Group IVB chloride, such as $SnCl_2$. More detailed descriptions of these catalyst complexes can be found in the applications Ser. No. 223,015 and 223,014. However, in all instances it should be realized that an excess (2 to 30 moles per mole of platinum or palladium) of the Group IVB halide should be present for superior results.

*See for example R. D. Cramer et al., J.A.C.S., 85,1691(1963)

While many of the above three component catalysts are disclosed to function as hydroformylation or carboxylation catalysts for various aliphatic olefins, the carboxylation of 1,5,9-cyclododecatriene to the cyclododecadienecarboxylate ester requires certain attributes that only certain members of said platinum or palladium catalyst classes possess.

These characteristics are:

1. The ability to carboxylate the heat sensitive 1,5,9-cyclododecatriene to the cyclododecadienecarboxylate ester (See Step 1 of Scheme I) at temperatures below 160° to 200°C, the operational range of many of the prior art Group VIII carboxyls used for carboxylation.
2. The ability to selectively carboxylate said triene to the desired monoester, with little or no production of the corresponding di- or triesters, and optionally
3. The ability to reduce the remaining two (2) double bonds of the cyclododecadienecarboxylate ester (See Step 2 of Scheme I) in a novel shortened process for preparing dodecyl (lauryl) lactam. This lactam is a favored precursor in the commercial preparation of the polyamide known as Nylon-12.

For the purposes of the first two steps, the catalysts may be selected from the group consisting of:

$PdCl_2[P(C_6H_5)_3]_2$-$SnCl_2$,
$PdCl_2[P(C_6H_5)_3]_2$-$GeCl_2$,
$PdCl_2[P(p-CH_3.C_6H_4)_3]_2$-$SnCl_2$,
$PdCl_2[P(p-CH_3O.C_6H_4)_3]_2$-$SnCl_2$,
$PdCl_2[P(C_6H_5)_3]_2$-$SnCl_4$,
$PtCl_2[P(C_6H_5)_3]_2$-$SnCl_2$, and
$PtCl_2[As(C_6H_5)_3]_2$-$SnCl_2$.

PRIOR ART

While no novelty search has been made, it is believed that the following is pertinent:

1. Bittler et al (Angew.Chem.Intern.Edit. 7,329 [1968]) proposed the use of the complex $PdCl_2[P(C_6H_5)_3]_2$ (without any Group IVB halide, such as $SnCl_2$, as applicant's claimed catalysts require) as catalysts to carboxylate 1,5,9-cyclododecatriene. Examples 1 and 2 of this application document that under virtually identical reaction conditions applicant's $SnCl_2$ complexes are superior to Bittler et al.'s catalysts lacking this Group IVB halide agent.
2. H. Itatani and J. C. Bailar [J.Am.Oil Chem. Soc., 44,147 (1967) and J.Am.Chem.Soc., 89,1592(1967)] have disclosed palladium and platinum catalysts including $PdCl_2[P(C_6H_5)_3]_2$-$SnCl_2$ for hydrogenating unsaturated fatty acid esters, particularly the methyl esters of unsaturated fatty acids found in soybean oil. However, insofar as is known, none of the published Prior Art teaches first carboxylating 1,5,9-cyclododecatriene with a selected group of the above empirically derived three component, ligand-stabilized platinum(II) or palladium(II)-Group IVB metal halide catalyst complexes in the presence of sufficient carbon monoxide and lower alkanol to produce the lower alkyl cyclododecadienecarboxylate, followed by a subsequent hydrogenation in the presence of the same platinum catalysts under mild reaction parameters of temperature and pressure.
3. U.S. patent applications Ser. Nos. 223,014 and 223,015 now U.S. Pat. No. 3,819,669 disclose the carboxylation of alpha and internal aliphatic monoolefins generally rather than the specific substrate 1,5,9-cyclododecatriene employed in this disclosure. Further, the specific catalysts of said application which are utilizable differ somewhat from the dual purpose claimed in this application. Finally, in the instant application both carboxylation and hydrogenation are achieved whereas in the applications only carboxylation takes place.

REACTION PARAMETERS FOR CARBOXYLATION

I. Temperatures and Pressures — The temperatures which can be used to carboxylate the aforementioned triene substrate are relatively narrow, ranging from about 60° to 90°C. In both instances the pressures can vary from 2000 psig to 4000 psig during carboxylation. Hydrogenation of the lower alkyl cyclododecadienecarboxylate intermediate requires similar parameters of temperature and superatmospheric pressures of hydrogen to produce a significant quantity of the completely saturated product within practical reaction times. Unexpectedly, palladium catalysts, such as $PdCl_2[P(C_6H_5)_3]_2$-$SnCl_2$, while highly active in carboxylating the 1,5,9-cyclododecatriene show little or no activity for the subsequent hydrogenation of the cyclododecadienecarboxylate ester within similar conditions of temperature and pressure.

II. Alkanol Coreactant — The alkanol coreactants which may be used in this invention include primary and secondary alcohols, phenol, substituted phenols, substituted alkanols and polyols. Preferred are primary alcohols containing 1 to 4 carbon atoms, including methanol, ethanol, n-propanol and iso-propanol.

III. Molar Ratio of 1,5,9-cyclododecatriene to palladium or platinum catalyst varies from 50 to 200 of said triene per mole of noble metal.

IV. Reaction Times are variable, depending upon the palladium or platinum catalyst employed, the reaction temperatures and pressures employed, and whether carboxylation or hydrogenation is the reaction carried out. In the former case, using $PdCl_2[P(C_6H_5)_3]_2$-$SnCl_2$ as a typical catalyst, the range of reaction times for carboxylation can take place between 1 and 24 hours when at least 50% conversion of the triene takes place. More typically the carboxylation of the triene takes place within 1 to 12 hours.

V. Inert Solvents — While inert solvents are not necessary for carboxylation nor hydrogenation, they do simplify handling of the components of the reaction mixture. For this reason solvents inert to both reactants, such as paraffins and aromatics and oxygenates such as ketones, in sufficient quantities to solubilize, or at least to disperse, the components, are employed. These include hexanes, heptanes, octanes, benzene, toluene, xylenes, methyl isobutyl ketone and the like.

VI. PROCESS SEQUENCE AND VARIATIONS

A. Carboxylation — In general, the components of the carboxylation mixture, including optional inert solvent, 1,5,9-cyclododecatriene and homogeneous, ligand stabilized, platinum(II) or palladium(II)-Group IVB metal halide catalyst complex, may be added in any sequence as long as good agitation of the reaction mixture and freedom from oxidizing agents or oxidizing atmosphere is provided. Process variations which can be employed include:

1. The homogeneous catalyst may be preformed in an inert environment and added preformed to deoxygenated inert solvent prior to the addition of the triene and other components such as the alkanol coreactant.
2. Preferably, to minimize stability problems, it is recommended that the catalyst complexes be formed in situ by mixing the deoxygenated inert solvent, alkanol reactant, and neat cyclododecatriene, followed by the addition of excess Group IVB metal halide, and finally by the addition of the ligand-stabilized platinum(II) or palladium(II) halide, such as $PtCl_2[As(C_6H_5)_3]_2$, to form the reaction mixture.
3. After employing variation (1) or (2) the reaction mixture of alkanol, inert solvent, catalyst (usually prepared in situ) and excess Group IVB metal halide and lacking only carbon monoxide, is sealed and pressurized using carbon monoxide and/or inert gas, initially only to low pressures ranging from about 10 psig to about 100 psig. After a homogeneous mixture is obtained, sufficient carbon monoxide is introduced to at least satisfy the stoichiometry needed for monocarboxylation of the triene, and to increase the superatmospheric pressure of the system up to about 2000 psig to 4000 psig. The pressurized reaction mixture is then heated until analysis indicates that the desired monocarboxylation of the triene has been obtained.

B. Hydrogenation

1. Order of adding reactants, catalyst and solvents. The reduction is ordinarily performed in a conveniently sized reactor of the type used for carboxylation under pressure. Generally degassed inert solvent(s) such as benzene or toluene, used as a vehicle for the preformed, ligand stabilized catalyst e.g. $PtCl_2[As(C_6H_5)_3]_2$, in combination with excess Group IVB catalyst component (such as $SnCl_2$), is charged to the reactor, as well as the alkyl cyclododecadiene carboxylate produced by carboxylation. During and after charging, the reactor is purged with inert gas such as nitrogen. The reactor is then sealed and heated under superatmospheric pressures provided by sufficient hydrogen gas to permit the desired reduction to take place. After monitoring the reduction with a suitable analytical technique, such as gas chromatography, the reduction is terminated by cooling the reactor and depressurizing it. The work-up is conventional and usually involves stripping off volatiles under vacuum, removing catalyst and utilizing chromatography, extraction etc. for further purification.

2. Reduction pressure — Generally superatmospheric pressures are required for reasonable rates of reduction at the desired temperature range. Ordinarily pressures ranging from about 500 psig and 2000 psig and higher are required.

3. Reduction temperatures — The hydrogenation reaction can be run between about 20° and 120°C with the best results being obtained between 60°C and 90°C.

In order to describe the inventive process in the greatest possible detail, the following illustrative embodiments are submitted.

EXAMPLE 1

Synthesis of Methyl Cyclododecadienecarboxylate from 1,5,9-cyclododecatriene

To a degassed sample of benzene (75 ml) and methanol (16 ml, 0.4 mole) contained in an appropriately sized, glass-lined reactor fitted with means of agitating, sampling, heating and pressurizing, is charged, under a nitrogen purge, 1.13 g. (5.0 mmole) of $SnCl_2.2H_2O$ followed by 0.35 g. (0.5 mmole) of $PdCl_2[P(C_6H_5)_3]_2$ previously pre-formed. The mixture is vigorously agitated for 3 to 5 minutes, while purging with nitrogen, to produce a clear red solution. The solution is then heated to 70°C under 100 psig of carbon monoxide, a solution of 8.1 g. (50.0 mmole) of 1,5,9-cyclododecatriene in 5 ml of deoxygenated benzene injected into the reactor, and the total pressure of the reaction mixture in the reactor raised to 2000 psig with additional carbon monoxide. The reactor is heated at 70°C under 2000 psig for 12 hours, and the course of the reaction followed by periodic sampling. At the end of this time, the reaction is terminated, the reactor cooled, vented free of gas, and 82 ml of light yellow liquid recovered. After purification by gas chromatography (g.c.), product samples were subject to analysis. Methyl cyclododecadienecarboxylate (a mixture of various isomers) was identified as the major product ester by IR, NMR and elemental analyses.

| ELEMENTAL Analyses<br>Calc. for $C_{12}H_{19}COOCH_3$ | Found |
|---|---|
| %C = 75.6 | 75.7 |
| %H = 10.0 | 9.9 |
| CHROMATOGRAPHIC ANALYSES | |
| 1,5,9-cyclododecatriene<br>conversion (mole %) | ≈50% |
| Methyl cyclododecadienecarboxylate | |

-continued

| ELEMENTAL Analyses Calc. for $C_{12}H_{19}COOCH_3$ | Found |
|---|---|
| Selectivity | 95% |
| Methyl cyclododecadiene-carboxylate yield (mole %) | 47% |

EXAMPLE 2

Synthesis of Methyl Cyclodedecadienecarboxylate from 1,5,9-cyclododecatriene using the Palladium Catalyst of Example 1 without the SnCl₂ Component In this example the techniques and experimental conditions of Example 1 are duplicated, but here the palladium catalyst is bis(triphenylphosphine)palladium(II) chloride alone, with no added tin(II) chloride cocatalyst. Gas chromatographic analysis of the product mixture reveals the following results:

| 1,5,9-cyclododecatriene conversion (mole %) | <30 |
|---|---|
| Methyl cyclododecadienecarboxylate selectivity | 94% |
| Methyl cyclododecadienecarboxylate yield (mole %) | 27 |

It is evident from a comparison of these data with those reported under Example 1 that, under comparable reaction conditions, the absence of SnCl₂ cocatalyst leads to lower conversions of 1,5,9-cyclododecatriene and lower yields of methyl cyclododecadienecarboxylate.

EXAMPLE 3

Synthesis of Methyl Cyclododecadienecarboxylate from Trans, Trans,Cis - 1,5,9-Cyclododecatriene In this example, the techniques, palladium catalyst, and experimental conditions of Example 1 are duplicated, but here the substrate is a single isomer of cyclododecatriene, namely trans, trans,cis-1,5,9-cyclododecatriene. Gas chromatographic analysis of the product mixture reveals the following results:

| 1,5,9-cyclododecatriene conversion (mole %) | 65 |
|---|---|
| methyl cyclododecadienecarboxylate yield (mole %) | 59 |
| trans, trans, cis-1,5,9-cyclododecatriene isomerization (mole %) | 8.6 |

EXAMPLES 4 TO 8

Synthesis of Ethyl Cyclododecadienecarboxylate from 1,5,9-Cyclododecatriene Using Various Ligand-Stabilized Platinum(II) and Palladium(II)-Group IVB Metal Halide Complexes as Catalyst In these examples, the selective carboxylation of 1,5,9-cyclododecatriene to ethyl*cyclododecadienecarboxylate is carried out using various combinations of ligand-stabilized platinum(II) and palladium(II) complexes with Group IVB metal halides under experimental conditions similar to those described in Example 1. The following complexes gave significant quantities of the desired ester:

$PdCl_2[P(C_6H_5)_3]_2$-$GeCl_2$
$PdCl_2[P(p-CH_3.C_6H_4)_3]_2$-$SnCl_2$
$PdCl_2[P(p-CH_3O.C_6H_4)_3]_2$-$SnCl_2$
$PdCl_2[P(C_6H_5)_3]_2$-$SnCl_4$
$PtCl_2[As(C_6H_5)_3]_2$-$SnCl_2$

*Obtained by substituting ethanol for methanol on a mole for mole basis

EXAMPLE 9

The Hydrogenation of Methyl Cyclododecadienecarboxylate

To a degassed sample of toluene (50 ml) contained in the reactor of Example 1 is charged, under a nitrogen purge, 0.95 g. (5.0 mmole) of SnCl₂, 0.44 g. (0.5 mmole) of $PtCl_2[As(C_6H_5)_3]_2$, previously prepared, and 2.1 g. of methyl cyclododecadienecarboxylate product of Example 1. The mixture is heated to 85°C under 500 psig of hydrogen for 12 hours, and the course of the reaction followed by periodic sampling. The reaction is then terminated by cooling the reactor and depressurizing, and 50 ml of reddish-brown liquid recovered. After purification by gas chromatography the sample was subjected to analysis. The major product is a mixture of methyl cyclododecenecarboxylate and methyl cyclododecanecarboxylate.

EXAMPLE 10

The Hydrogenation of Ethyl Cyclododecadienecarboxylate

In this example, the hydrogenation technique of Example 9 is repeated under similar conditions of temperature and H₂ pressure, but here the reaction charge is the product of Example 8, consisting of inert solvent, benzene, platinum catalyst, $PtCl_2[As(C_6H_5)_3]_2$-$SnCl_2$, and ethyl cyclododecadienecarboxylate ester.

The major ester product of hydrogenation is a mixture of ethyl cyclododecenecarboxylate and ethyl cyclododecanecarboxylate.

As the several examples and previous discussion indicate, both process aspects of this invention are novel and advantageous. For example, the present commercial processes for preparing Nylon-12 precursor require more steps and processing operations and necessitates the preparation of unstable intermediates such as cyclododecanone oxime.

In contrast, applicant's novel process utilizes a single, dual purpose catalyst for both carboxylation and the reduction steps, requires fewer steps and less processing operations and employs relatively mild conditions of temperature and pressure.

Similarly, the claimed carboxylation of 1,5,9-cyclododecatriene to produce alkyl cyclododecadienecarboxylate employs several heretofore undescribed homogeneous, ligand stabilized platinum-(II) or palladium(II)-Group IVB metal halide catalyst complexes, which exhibit good selectivity, produce the desired monocarboxylated product in good yield yet do not require severe reaction conditions.

Other advantages and applications of the inventive concepts will become apparent to those skilled in the art after a perusal of the claims which follow in view of the specification.

What is claimed is:
1. A process for preparing monoalkyl cyclododecanecarboxylates, said monoalkyl radicals being selected from the group consisting of methyl and ethyl, from 1,5,9-cyclododecatriene, by the process of:
   a. contacting each molar equivalent of 1,5,9-cyclododecatriene present with from about 0.005 to 0.02 molar equivalents of $PtCl_2[As(C_6H_5)_3]_2$-$SnCl_2$ and at least one molar equivalent of an alkanol selected from the group consisting of methanol and ethanol, in an oxygen-free inert solvent, in the presence of a pressurized carbon monoxide atmosphere of from about 2000 psig to 4000 psig, to form a pressurized carboxylation mixture, b. heating said pressurized carboxylation mixture between about 60° to 90°C, until substantial monocarboxylation of said triene takes place, and monoalkyl cyclododecadienecarboxylate is prepared, c. removing the carbon monoxide from the carboxylation mixture containing the monoalkyl cyclododecadienecarboxylate, and contacting each molar equivalent of said cyclododecadienecarboxylate present, in an oxygen-free inert solvent environment with about 0.005 to 0.02 molar equivalents of $PtCl_2[As(C_6H_5)_3]_2$-$SnCl_2$, under a pressurized hydrogen atmosphere ranging from about 500 psig to 2000 psig to form a pressurized hydrogenation mixture, d. heating said pressurized hydrogenation mixture between about 60° and 90°C, until substantial hydrogenation to the monoalkyl cyclododecanecarboxylate ester takes place, and e. isolating the monoalkyl cyclodedecanecarboxylate ester contained therein.

2. The process of claim 1 wherein the monoalkyl radical of the monoalkyl cyclododecanecarboxylates is methyl.

3. The process of claim 1 wherein the monoalkyl radical of the monoalkyl cyclododecanecarboxylate is ethyl.

4. The process of claim 1 wherein the inert solvent is an aromatic solvent selected from the group consisting of benzene, toluene and the xylenes.

* * * * *